United States Patent
Roy et al.

(10) Patent No.: US 9,534,037 B2
(45) Date of Patent: Jan. 3, 2017

(54) SYSTEMS AND METHODS TO INCREASE PROTEIN YIELD FROM RECOMBINANT MANUFACTURING PROCESSES

(75) Inventors: Sylvain Roy, Santa Monica, CA (US); Ganesh Vissvesvaran, Fremont, CA (US)

(73) Assignees: Baxalta GmbH, Opfikon (CH); Baxalta Incorporated, Bannockburn, IL (US)

(*) Notice: Subject to any disclaimer, the term of this patent is extended or adjusted under 35 U.S.C. 154(b) by 456 days.

(21) Appl. No.: 13/565,046

(22) Filed: Aug. 2, 2012

(65) Prior Publication Data

US 2013/0034876 A1  Feb. 7, 2013

Related U.S. Application Data

(60) Provisional application No. 61/632,399, filed on Aug. 2, 2011.

(51) Int. Cl.

| | | |
|---|---|---|
| *A23J 1/00* | (2006.01) | |
| *C07K 1/00* | (2006.01) | |
| *C07K 14/00* | (2006.01) | |
| *C07K 16/00* | (2006.01) | |
| *C07K 17/00* | (2006.01) | |
| *C12P 21/06* | (2006.01) | |
| *C07K 14/755* | (2006.01) | |
| *C07K 1/34* | (2006.01) | |

(52) U.S. Cl.
CPC ............... *C07K 14/755* (2013.01); *C07K 1/34* (2013.01)

(58) Field of Classification Search
CPC .................. C07K 14/755; C07K 1/34
See application file for complete search history.

(56) References Cited

U.S. PATENT DOCUMENTS

| | | | |
|---|---|---|---|
| 6,759,215 B1 * | 7/2004 | Zsebo et al. | 435/69.5 |
| 2006/0199948 A1 | 9/2006 | Ejima et al. | |
| 2013/0017997 A1 * | 1/2013 | Schellenberger et al. | 514/14.1 |

FOREIGN PATENT DOCUMENTS

| | | | |
|---|---|---|---|
| EP | 1820555 A1 | 8/2007 | |
| WO | 2003/100080 A2 | 12/2003 | |
| WO | 2008/091740 A2 | 7/2008 | |
| WO | WO 2008/135568 | * 11/2008 | ........... C07K 14/755 |
| WO | 2013/019964 A1 | 2/2013 | |

OTHER PUBLICATIONS

Necina et al., Peptide affinity chromatography of human clotting factor VIII Screening of the vWF-binding domain, Journal of Chromatography B, 715 (1998) 191-201.*
Sawatani et al., A chromatographic method for the production of a human immunoglobulin G solution for intravenous use, Braz J Med Biol Res 31(11), 1375-1381.*

(Continued)

*Primary Examiner* — Reza Ghafoorian
(74) *Attorney, Agent, or Firm* — K&L Gates LLP; Louis C. Cullman; Georgia N. Kefallinos

(57) ABSTRACT

Embodiments disclosed herein provide systems and methods that increase protein yield from recombinant manufacturing processes. The systems and methods treat used depth filters with bound proteins of interest as a stationary phase exchange resin to recapture bound protein of interest from the depth filter.

13 Claims, 2 Drawing Sheets

(56) References Cited

OTHER PUBLICATIONS

Firer et al., Efficient elution of functional proteins in affinity chromatography, J. Biochem. Biophys. Methods 49 Ž2001. 433-442.*

Gomperts et al., The manufacturing process of recombinant factor VIII, recombinate. Transfusion Medicine Reviews, vol. 6, No. 4, pp. 247-251 (1992).

International Search Report mailed on Nov. 20, 2012 for International Application No. PCT/US2012/049357 filed on Aug. 2, 2012.

Kandula et al., Design of a filter train for precipitate removal in monoclonal antibody downstream processing. Biotechnolgy and Applied Biochemistry, vol. 54, No. Part 3, pp. 149-155 (2009).

Kolind et al., Optimisation of the Factor VIII yield in mammalian cell cultures by reducing the membrane bound fraction. Journal of Biotechnology, vol. 151, No. 4, pp. 357-362 (2011).

Levesley et al., The effect of high frequency backflushing on the microfiltration of yeast homogenate suspeensions for the recovery of soluble proteins. Journal of Membrane Science, vol. 158, No. 1-2, pp. 29-39 (1999).

Saxena et al., Membrane-based techniques for the separation and purification of proteins: An overview. Advances in Colloid and Interface Science, vol. 145, No. 1-2, pp. 1-22 (2009).

Shukla et al., Recent advances in large-scale production of monoclonal antibodies and related proteins. Trends in Biotechnology, vol. 28, No. 5, pp. 253-261 (2010).

Van Reis et al., Bioprocess membrane technology. Journal of Membrane Science, vol. 297, No. 1-2, pp. 16-50 (2007).

Yigzaw et al., Exploitation of the adsorptive properties of depth filters for host cell protein removal during monoclonal antibody purification. Biotechnology Progress, vol. 22, No. 1, pp. 288-296 (2006).

Van Holten et al., Evaluation of depth filtration to remove prion challenge from an immune globulin preparation. Vox Sanguinis vol. 85, pp. 20-24 (2003).

* cited by examiner

SYSTEMS AND METHODS TO INCREASE PROTEIN YIELD FROM RECOMBINANT MANUFACTURING PROCESSES

PRIORITY CLAIM

This patent application claims priority pursuant to 35 U.S.C. §119(e) to U.S. Provisional Patent Application Ser. No. 61/632,399 filed Aug. 2, 2011, which is hereby incorporated by reference in its entirety.

FIELD OF THE DISCLOSURE

Disclosed herein are systems and methods that increase protein yield from recombinant manufacturing processes. The systems and methods treat used depth filters with bound proteins of interest as a stationary phase exchange resin to recapture bound protein of interest from the depth filter.

BACKGROUND OF THE DISCLOSURE

The use of recombinantly-produced therapeutic proteins has continued to increase in treating many diseases and conditions. For example, Factor VIII is a trace plasma glycoprotein that is found in mammals and is involved as a cofactor in the activation of Factor X and Factor IXa. An inherited deficiency of Factor VIII results in the bleeding disorder hemophilia A, which can be treated successfully by administration of recombinant Factor VIII.

Recombinant Factor VIII (rFVIII) can be produced by Chinese Hamster Ovary (CHO) cells transfected with a vector carrying a DNA sequence encoding the Factor VIII molecule. In some cases, rFVIII is co-produced with recombinant von Willebrand Factor (rvWF). As stated, these recombinantly-produced proteins can provide an effective treatment for hemophilia.

Conventional methods of recombinantly producing proteins involve inserting the gene responsible for the production of a particular protein of interest into host cells such as bacteria, yeast, or mammalian cells, e.g., COS or CHO cells, and then growing the cells in culture media. The cultured cells then synthesize the protein of interest. Traditional bacteria or yeast systems can be unable to produce many complex proteins in a functional form. While mammalian cells can reproduce complex proteins, they are generally difficult and expensive to grow, and often produce only mg/L quantities of protein. In addition, non-secreted proteins are relatively difficult to purify from prokaryotic or mammalian cells as they are not secreted into the culture medium. Accordingly, while recombinantly-produced therapeutic proteins can provide therapeutic benefits to a large number of diseases and conditions, the large-scale production of these proteins remains a challenge.

Regarding recombinant Factor VIII, particularly, this protein is expensive to produce due to the relatively low yields obtained in processes known in the art. The yield per cell tends to be low compared to the yield that might be obtained for other recombinant proteins. Generally, secreted FVIII is separated from source CHO cells, debris and DNA using depth filtration that employs charged CUNO filters. The charged depth filter binds to the FVIII product thereby reducing the final recovery of the protein.

Based on the foregoing, new techniques that enhance production and recovery of recombinantly-produced therapeutic proteins are needed.

SUMMARY OF THE DISCLOSURE

The present disclosure provides systems and methods that increase protein yield from recombinant manufacturing processes. In particular embodiments, the systems and methods treat used depth filters with bound proteins of interest as a stationary phase exchange resin to recapture bound protein of interest using a high salt elution buffer. By increasing protein yield from recombinant manufacturing process, these systems and methods improve the efficiency and cost of manufacturing therapeutic proteins.

Particularly, one embodiment includes a method of increasing the amount of a protein of interest available for recovery from a sample containing other components and following a first purification step of the sample comprising: exposing a filter through which the sample has been passed to an elution buffer wherein exposure to the elution buffer releases the protein of interest from the filter for subsequent recovery.

Another embodiment further includes recovering the released protein of interest from the elution buffer.

In another embodiment, the elution buffer is a salt elution buffer.

In another embodiment, the elution buffer has a conductivity of at least 20 mS/cm.

In another embodiment, the filter is positively-charged.

In another embodiment, the filter is a depth filter.

In another embodiment, the protein of interest is a therapeutic protein. In another embodiment, the protein of interest is FVIII. In another embodiment, the protein of interest is rFVIII.

Another embodiment includes a method of manufacturing and recovering a protein of interest comprising: recombinantly producing a protein of interest using a host cell within a medium; filtering the medium using depth filtration; exposing the depth filter to an elution buffer to release protein of interest from the filter; recovering released protein of interest from the elution buffer; and recovering further protein of interest from the sample passed through the depth filter.

In another embodiment, the elution buffer is a salt elution buffer.

In another embodiment, the elution buffer has a conductivity of at least 20 mS/cm.

In another embodiment, the filter is positively-charged.

In another embodiment, the recombinantly-produced protein of interest is a therapeutic protein. In another embodiment, the recombinantly-produced protein of interest is rFVIII.

Another embodiment further includes combining the protein of interest recovered from the elution buffer and the protein of interest recovered from the sample passed through the depth filter into a pharmaceutical composition with pharmaceutically acceptable carriers.

Another embodiment includes a method of manufacturing a pharmaceutical composition comprising: recombinantly producing a therapeutic protein of interest using a host cell within a medium; filtering the medium using a CUNO depth filter with a positive charge; exposing the depth filter to a salt elution buffer with a conductivity of at least 20 mS/cm to release protein of interest from the filter; recovering released protein of interest from the salt elution buffer; recovering further protein of interest from the sample passed through the depth filter; and combining recovered protein of interest with pharmaceutically acceptable carriers thereby forming the pharmaceutical composition.

In another embodiment, the salt elution buffer has a conductivity of at least 30 mS/cm.

In another embodiment, the salt elution buffer has a conductivity of at least 50 mS/cm.

In another embodiment, the protein of interest is recombinantly-produced rFVIII.

DETAILED DESCRIPTION OF THE DISCLOSURE

Figure 1:
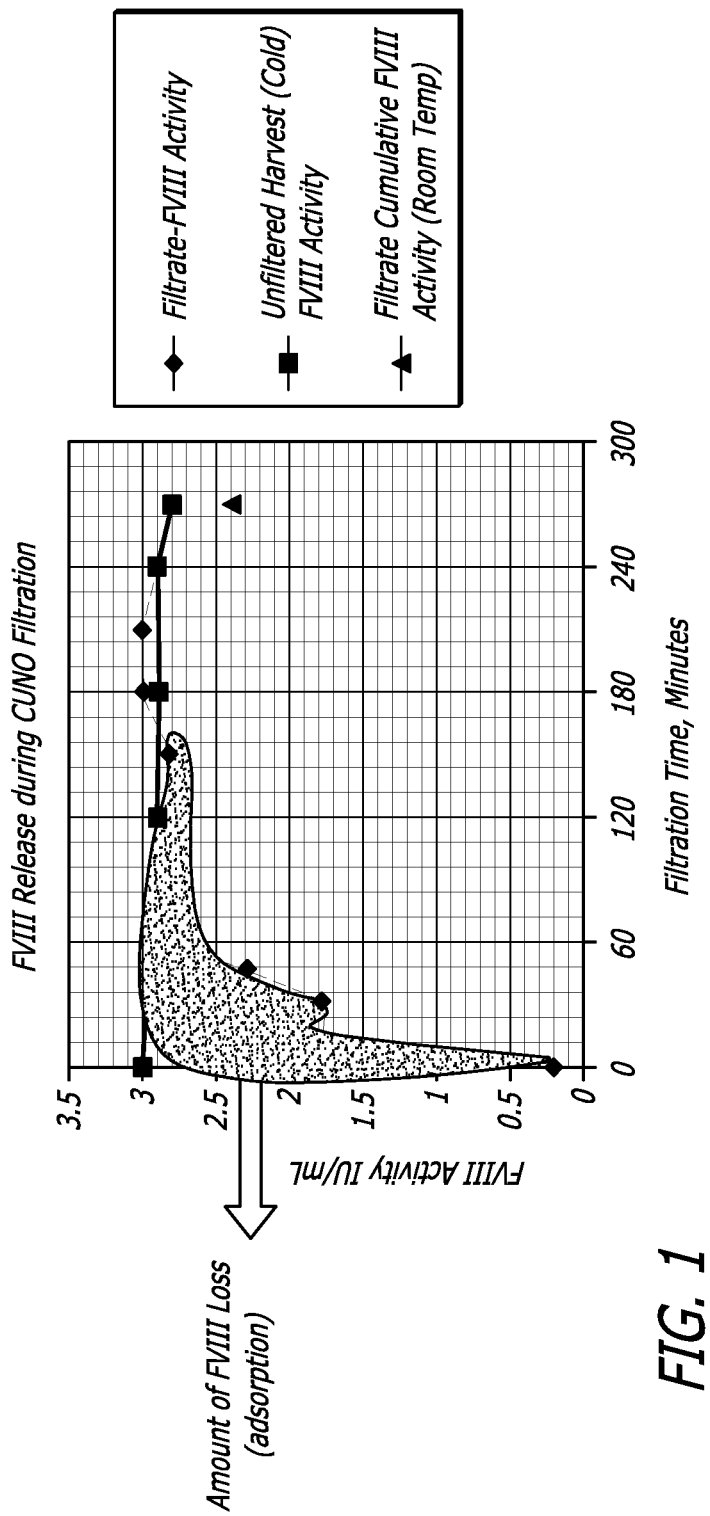
FIG. 1 shows that during initial media filtration following recombinant production, rFVIII binds to a depth filter membrane until the first hour of filtration has passed and that the quantity of product lost due to such binding is approximately 10%.

A growing number of recombinant proteins are being developed for therapeutic and diagnostic applications. Many of these proteins can be difficult or expensive to produce, however, in required quantities using conventional methods.

Embodiments disclosed herein include systems and methods for increasing recovery of a protein of interest following recombinant production. In recombinant production, proteins of interest are secreted from host cells into surrounding culture medium. As a non-limiting example, in a typical process for preparing recombinant Factor VIII, recombinant host cells are cultured in a medium and secrete Factor VIII into the medium.

The term "recombinant host cell" (or simply "host cell"), as used herein, refers to a cell into which a recombinant expression vector has been introduced. It should be understood that such terms are intended to refer not only to the particular subject cell but to the progeny of such a cell. Because certain modifications can occur in succeeding generations due to either mutation or environmental influences, such progeny may not, in fact, be identical to the parent cell, but are still included within the scope of the term "host cell" as used herein.

In embodiments disclosed herein, the most common host cell is a Chinese Hamster Ovary (CHO) cell. Other types can also be used, however, including, without limitation, all appropriate prokaryote and eukaryote cells, including bacterial, yeast, fungi, insect and mammalian cells. Hosts include microbial cells, especially microorganisms like E. coli. Any suitable strain of E. coli is contemplated. Likewise, genes encoding diverse structural proteins (or peptides, polypeptides, glycoproteins, phosphoproteins, amidated proteins, etc.) can be inserted into the expression vector, which genes can constitute genomic DNA, cDNA, synthetic DNA, polynucleotide and oligonucleotide, etc. These nucleic acids can be obtained using chemical synthesis or gene manipulation techniques (see Sambrook, Fritsch, Maniatis, Molecular Cloning, A Laboratory Manual, Second Edition, Cold Spring Harbor Laboratory Press, 1989; and Current Protocols in Molecular Biology, Greene Publishing Assoc. & Wiley, 1987) and, further, can be inserted into expression vectors, and the expression vectors subsequently introduced into host cells using additional gene manipulation techniques (id.).

Introduction of the expression vector into a host cell can be effected by, without limitation, heat shock, calcium phosphate transfection, DEAE-Dextran mediated transfection, or electroporation (Hanahan, D., J. Mol. Biol. 166:557-580 (1983); Davis, L. et al., Basic Methods in Molecular Biology (1986)).

Culturing of an expression vector containing host can be carried out using known processes such as those disclosed in the aforementioned documents, and include, but are not limited to, the use of incubators, bioreactors, fermentors etc., according to batch fermentation, fed batch fermentation, continuous culture, Type I, II and III fermentation, aseptic fermentation, consortium fermentation, protected fermentation, etc. Fitting the conditions (e.g., medium, temperature, pH, hours, agitation, aeration, etc.) for culture to the circumstances is empirical and within the ordinary skill of those in the art.

Following production, the protein or proteins of interest must be separated from the host cell media and other impurities such as cellular debris, nucleic acids, RNA, protein, endotoxins, pyrogens and host chromosomal DNA. In one embodiment Factor FVIII is the protein of interest that is separated and purified from the medium. In another embodiment, the protein or proteins of interest are Factor VIII complexed with vWF.

Depth filtration is often employed as a purification step to separate host cells and other impurities from a protein of interest. Depth filters are generally formed with a matrix of multi-directional fibers forming tortuous passages so that they are capable of trapping and retaining particles that are smaller than their pore size. A depth filter accomplishes this type of filtration at least partly because fluid passing through the filter media is caused to change direction as it passes through the multi-directional fibers. This in turn causes very fine particulate material in the liquid to be deposited and retained in niches or crevices even though the particles can be smaller than the openings in the media. Accordingly, this type of filter is capable of retaining particles from a mobile liquid phase throughout the filter rather than just on the surface of the filter.

Depth filters can also be charge-modified. A charge-modified depth filter typically has two distinct zones and, thus, two distinct mechanisms for the removal of contaminants. The first is the physical means of capture of contaminant where particles become entrapped within the matrix as described above. The second is electrokinetic absorption which removes contaminants of an opposite charge. The two or more zones or layers can be composed of similar materials (in which the materials are formulated and processed such that they have different retention capabilities), or can be composed of different materials having distinctly different particle retention characteristics. The two or more zones can be contiguous or non-contiguous with one another as long as the fluid being filtered communicates between the zones.

Depth filters can be composed of numerous materials including, without limitation, a fibrous bed of cellulose or polypropylene fibers, fiber mats, woven or nonwoven fabrics, or a synthetic fabric, such as nylon or rayon, e.g., Miracloth® (Calbiochem, La Jolla, Calif.) along with a filter aid or "matrix", e.g., paper, plastic, metal, glass, glass fibers, nylon, polyolefin, carbon, ceramics, diatomaceous earth, cellulose or diatomite (skeletal remains of minute algae (diatoms) found in marine deposits that have lifted above sea level).

Charge-depth filters are manufactured by numerous companies, including, for example, Cuno, Inc., ErtelAlsop, Filtrox AG, GE Infrastructure Water and Process Technologies, Meissner Filtration Products, Inc., Millipore Corp., Pall, Corp., Sartorius AG, and US Filter. Several product lines of charge-depth filters are available from all of these companies. Non-limiting examples of such charge-depth filters include, ZetaPlus, PolyNET, Betafine, Disk-Pak, Accusclae, PharmaScale, PuraFix.

Particular embodiments disclosed herein employ CUNO 30SP filters that contain cellulose, fiberaid, and a resin that imparts a positive charge to the filter surfaces. These filters contain significant voids volume which allow for accumulation of cellular debris. The filter structure is a series of interconnecting pore pathways able to retain cellular debris by mechanical entrapment. In addition to debris removal by mechanical retention, Zeta Plus filters are also able to remove particles smaller than their pore size. This capability is based on electrokinetic attraction of negatively charged particles by the positively charged filter surfaces. DNA, which is a polyanionic negatively charged molecule, would also be removed by these filters. Negatively-charged proteins of interest, however, such as rFVIII at a pH of 7 also bind to the filters reducing recovery and yield from the filtration process.

Embodiments disclosed herein provide systems and methods to recapture protein of interest bound by a depth filter during purification processes. Particular embodiments of the systems and methods disclosed herein utilize a pseudo chromatographic method to release the bound protein of interest from the depth filters using a gradient of a high salt elution buffer. Accordingly, protein of interest captured by the depth filter can be recaptured by contacting the depth filter with an elution buffer, in one embodiment, a high salt elution buffer and in a further embodiment an inorganic high salt elution buffer comprising sodium chloride. These methods can be accomplished using a variety of techniques including bathing, soaking, or dipping a depth filter to which the protein of interest is bound into the elution buffer, or by rinsing, spraying, or washing the elution buffer over the depth filter. Such treatments will release the protein of interest from the depth filter so that it can then be recaptured, increasing yield of the recombinant manufacturing process.

Non-limiting exemplary elution buffers include nuclease-free water, aqueous solutions such as, TRIS™-HCl or TRIS™-ethylenediaminetetraacetic acid (EDTA) or a solution that contains one or more of piperadine, imidazole or o-phosphate. Elution buffers can also be aqueous solutions that include, without limitation, ammonium carbonate, ammonium hydroxide, diammonium citrate, ammonium acetate, ammonium dihydrogen phosphate, or ammonium bicarbonate.

High salt elution buffers are those that have sufficient ionic strength to mask charge characteristics of the protein of interest and depth filter so that captured protein of interest is eluted from the depth filter. Salts having multi-valent ions are particularly useful in this regard, e.g., sulphates and phosphates with alkali earth or transition metal counterions, although salts dissociating to one or more monovalents are also suitable for use within embodiments disclosed herein. Accordingly, non-limiting appropriate elution buffer salts include alkali metal, alkaline earth metal and/or ammonium salts, as well as citrate, phosphate, borate, lactate and the like salts and mixtures thereof.

Elution buffers described herein can have a conductivity of at least 20 mS/cm, at least 30 mS/cm, at least 40 mS/cm, at least 50 mS/cm, at least 60 mS/cm, at least 70 mS/cm, at least 80 mS/cm, at least 90 mS/cm, at least 100 mS/cm, at least 110 mS/cm, at least 120 mS/cm, at least 130 mS/cm, at least 140 mS/cm, at least 150 mS/cm, at least 160 mS/cm, at least 170 mS/cm, at least 180 mS/cm, at least 190 mS/cm, at least 200 mS/cm, at least 210 mS/cm, at least 220 mS/cm, at least 230 mS/cm, at least 240 mS/cm, at least 250 mS/cm, at least 260 mS/cm, at least 270 mS/cm, at least 280 mS/cm, at least 290 mS/cm, at least 300 mS/cm, at least 310 mS/cm, at least 320 mS/cm, at least 330 mS/cm, at least 340 mS/cm, at least 350 mS/cm, at least 360 mS/cm, at least 370 mS/cm, at least 380 mS/cm, at least 390 mS/cm, or at least 400 mS/cm.

The systems and methods disclosed herein can be applied to any therapeutic protein, including erythropoietin, darbepoietin, granulocyte-colony stimulating factor, or an antibody.

Other examples of proteins include granulocyte-colony stimulating factor (GCSF), stem cell factor, leptin, hormones, cytokines, hematopoietic factors, growth factors, antiobesity factors, trophic factors, anti-inflammatory factors, receptors or soluble receptors, enzymes, variants, derivatives, or analogs of any of these proteins. Other examples include insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferons (alpha, beta, gamma), interleukins (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakaryocyte derived growth factor (MGDF), keratinocyte growth factor (KGF), thrombopoietin, platelet-derived growth factor (PGDF), colony simulating growth factors (CSFs), bone morphogenetic protein (BMP), superoxide dismutase (SOD), tissue plasminogen activator (TPA), urokinase, streptokinase, or kallikrein, receptors or soluble receptors, enzymes, variants, derivatives, or analogs of any of these proteins.

Proteins of interest also include coagulation factors such as, and without limitation, FVIII, FVIIa, FIX, VWF, FV, FX and FXIII.

Exemplary antibodies include Herceptin® (Trastuzumab), a recombinant DNA-derived humanized monoclonal antibody that selectively binds to the extracellular domain of the human epidermal growth factor receptor 2 (Her2) proto-oncogene; and Rituxan® (Rituximab), a genetically engineered chimeric murine/human monoclonal antibody directed against the CD20 antigen found on the surface of normal and malignant B lymphocytes. Other exemplary antibodies include Avastin® (bevacizumab), Bexxar® (Tositumomab), Campath® (Alemtuzumab), Erbitux® (Cetuximab), Humira® (Adalimumab), Raptiva® (efalizumab), Remicade® (Infliximab), ReoPro® (Abciximab), Simulect® (Basiliximab), Synagis® (Palivizumab), Xolair® (Omalizumab), Zenapax® (Daclizumab), Zevalin® (Ibritumomab Tiuxetan), or Mylotarg® (gemtuzumab ozogamicin), Vectibix® (panitumumab), receptors or soluble receptors, enzymes, variants, derivatives, or analogs of any of these antibodies.

One embodiment disclosed herein is for the recovery of blood clotting factor VIII (Factor VIII).

As will be understood by one of ordinary skill in the art, the systems and methods disclosed herein can beneficially be used with additional filtering and capture techniques such as, and without limitation, affinity chromatography, size exclusion chromatography, gel filtration, cation-exchange chromatography, anion-exchange chromatography, hydrophobic-interaction chromatography, ceramic hydroxyapatite chromatography, reverse-phase HPLC and/or chromatofocusing to fully isolate and purify the protein of interest to accepted pharmaceutical standards.

The systems and methods disclosed herein can be incorporated into scalable unit operations allowing the production of milligram, gram and kilogram quantities of a protein of interest.

Purified proteins of interest can be incorporated into pharmaceutical compositions suitable for administration to a subject. Typically, the pharmaceutical composition comprises a therapeutic protein and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is known in the art. Except insofar as any conventional media or agent is incompatible with the active protein of interest, use thereof in the compositions is provided. Supplementary active compounds can also be incorporated into the compositions.

Pharmaceutical compositions are formulated to be compatible with the intended route of administration. Examples of routes of administration include parenteral, e.g., intravenous, intradermal, subcutaneous, oral (e.g., inhalation), transdermal (topical), transmucosal, and rectal. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and fluid to the extent that easy syringeability exists. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, a binding molecule is prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those of ordinary skill in the art. The materials can also be obtained commercially from Alza Corporation and Nova Pharmaceuticals, Inc. Liposomal suspensions can also be used as pharmaceutically acceptable carriers. These can be prepared according to methods known to those of ordinary skill in the art, for example, as described in U.S. Pat. No. 4,522,811.

The pharmaceutical compositions can be included in a container, pack, or dispenser together with instructions for administration.

This invention is further illustrated by the following examples, which should not be construed as limiting.

EXAMPLES

The following non-limiting examples are provided for illustrative purposes only in order to facilitate a more complete understanding of representative embodiments now contemplated. These examples should not be construed to limit any of the embodiments described in the present specification.

Example 1

A 5 liter continuous culture was established in a glass bioreactor, using a CHO cell line transformed to co-express Factor VIII and von Willebrand Factor. A suitable cell line is disclosed in U.S. Pat. Nos. 5,250,421 and 6,100,061 both of which are incorporated by reference herein for their teachings regarding the same. The culture medium was:

| | |
|---|---|
| DMEM/Ham's F12 50/50 | 11.76 g/kg |
| L-glutamine | 0.6 g/kg |
| Ethanolamine | 1.53 mg/kg |
| Synperonic F68 | 0.25 g/kg |
| NaHCO$_3$ | 2 g/kg 4 g/kg |
| Soya peptone C | 17.02 µg/kg (ppb) |
| CuSO$_4$•5H$_2$O | (includes constant contribution of 1.3 mg/kg from DMEM/F12 powder). This corresponds to 4.3 ppb copper in medium (nb: ratio MW CuSO$_4$•5H$_2$O/MW Cu = 3.931.) |

Example 2

A scaled down version of the depth filter used at appropriate production scales was used in the Examples described herein. Based on the principle of maintaining the cell culture harvest flux of 101 L/m2/hr, the flow rate required for a scaled down 25 cm$^2$ depth filter was calculated to be 4 mL/min.

A CUNO 30SP filter containing cellulose, fiberaid and a resin that imparts a positive charge to the filter's surfaces was flushed with 500 mL water for injection and autoclaved for 30 minutes at 123 C. to simulate the steam in place process employed for production filters. Further the filter was purged with air to remove any traces of water that could dilute the product released during the initial stages of the filtration.

The cell culture harvest from the model 5 L bioreactor process of Example 1 was filtered through the small scale filters. The filtered cell culture supernatant was collected at regular time intervals (0, 5, 15, 30, 60 240 minutes). These samples were subsequently analyzed for their rFVIII content using standard procedures to quantify the release of rFVIII from the filter membrane. During this test that was repeated at least 7 times, rFVIII was found to bind to the filter membrane until the first hour of filtration had passed. The quantity of product lost due to such binding was determined to be approximately 10% (FIG. 1).

Example 3

Depth filters used in Example 2 procedures were treated as a chromatographic column and the bound rFVIII was recovered. Particularly, a pseudo chromatographic method was devised where the filter membrane, containing bound protein of interest (rFVIII) and other impurities (host cell proteins, DNA etc) was treated as a stationary phase. More particularly, the positively-charged depth filter had bound the negatively-charged protein of interest, acting as an anionic exchange resin. A high salt elution DO2 buffer was used to preferentially unbind the protein of interest (rFVIII) thereby releasing it from the matrix of the depth filter.

The DO2 buffer is rich in sodium chloride salt (4M) with a conductivity of above 400 mS/cm. The buffer was diluted to 100 mS/cm using Water For Injection. The DO2 buffer can also be used to cleave rFVIII-vWF complexes that are obtained due to co-culturing of both proteins in the protein expression.

An AKTA pilot skid with consists of pumps for fluid handling and control, online pH, conductivity, UV detectors, flow path and fraction collector was used to recover the bound rFVIII. The small scale filter was used as the column with the filter membrane acting as the stationary phase and DO2 buffer as the mobile phase.

A slow elution gradient of the diluted DO2 buffer at a flow rate of 4 mL/min was employed on the small scale 25 cm$^2$ depth filters ranging from a low to 10 mS/cm to a high of 100 mS/cm. It should be noted that the conductivity of the cell culture harvest was 17 mS/cm. Therefore, a lower conductivity will essentially wash away the unbound rFVIII product and debris. This fraction could be collected separately and pooled later depending upon the recovered product amount.

Figure 2:
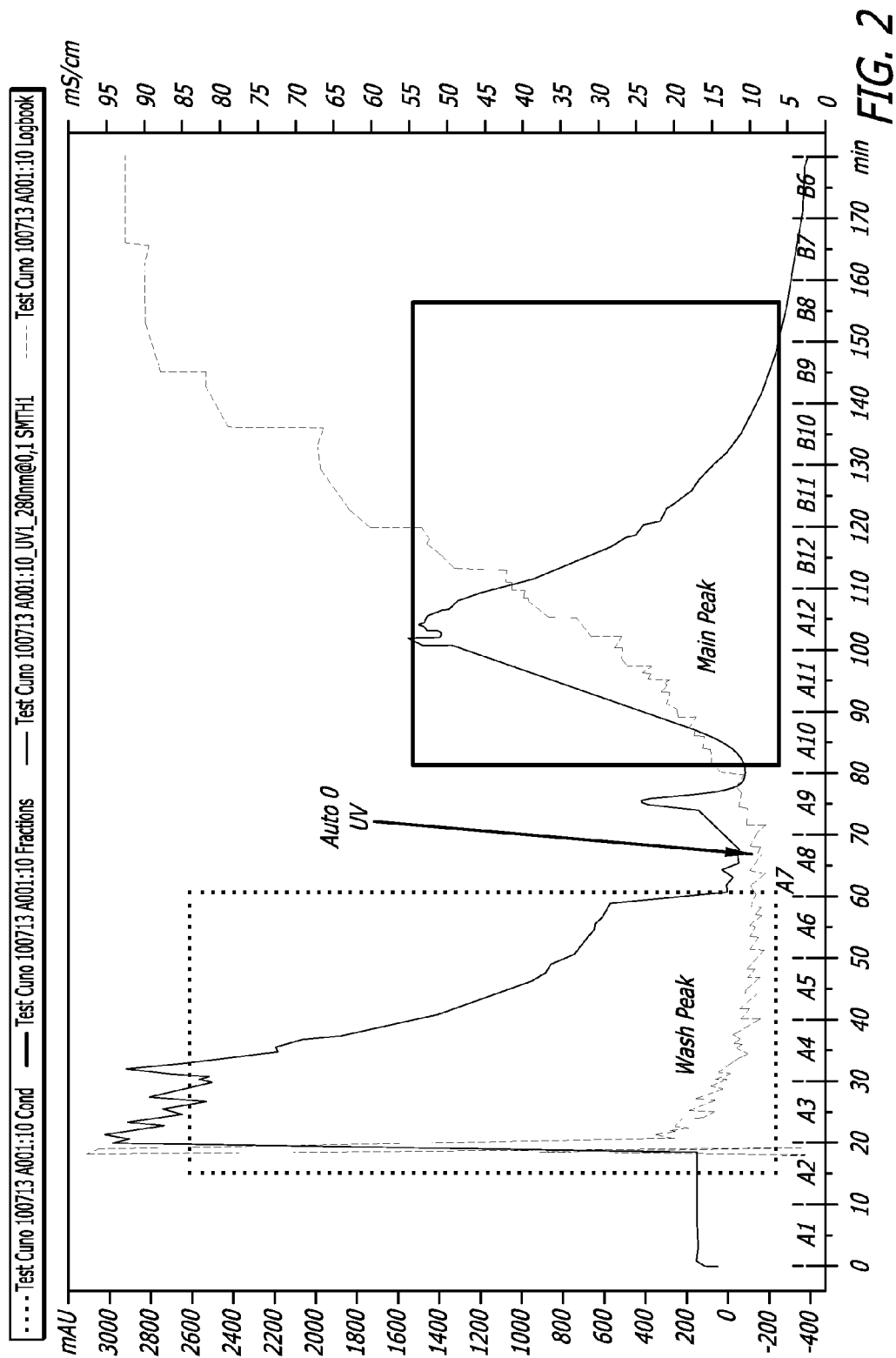
FIG. 2 shows that release of rFVIII captured by a depth filter requires use of an elution buffer with a threshold conductivity of 20 mS/cm.

As the conductivity increased during the gradient, the amount of UV absorbance also increased indicating that the bound rFVIII was slowly getting released from the filter matrix. Smaller fractions of 10 mL volumes were collected and analyzed for their rFVIII and impurity content. The peak absorbance occurred around a conductivity of 50 mS/cm and the release of rFVIII required a threshold conductivity of 20 mS/cm (FIG. 2).

The UV absorbance peak observed with the gradient of the 100 mS/cm DO2 buffer seemed to coincide with a proportional release of rFVIII in the "eluted" fractions. The fraction yielded a cumulative increase of 4.4% of rFVIII in the final pool mixed with the clarified cell culture supernatant obtained from the depth filtration process as seen in the Table 1 below.

TABLE 1

| Collection Type | Volume Collected (mL) | FVIII Activity (IU) | CHO-HCP (µg) | BiP (µg) | CHO-DNA (pg) | Total Protein (mg) | vWF (µg) |
|---|---|---|---|---|---|---|---|
| Depth filtration only | 840 | 2352 | 19891.2 | 4536 | 42840000 | 1114.68 | 5880 |
| Depth filtration only plus Chromatography | 1000 | 2456 | 25798.1 | 5659 | 409485000 | 1131.41 | 5911 |
| % Increase | 19.0 | 4.4 | 29.7 | 24.8 | 855.8 | 1.5 | 0.5 |

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. A method of increasing the amount of a protein of interest available for recovery from a sample containing other components and following a first purification step of the sample comprising:
    passing the sample through a depth filter;
    creating a chromatographic column wherein the depth filter is treated as a stationary phase;
    exposing the depth filter to an elution buffer wherein exposure to the elution buffer releases the protein of interest from the depth filter for subsequent recovery, wherein the protein of interest is Factor VIII, and wherein the elution buffer has a conductivity of at least 20 mS/cm.

2. A method of claim 1 further comprising: recovering the released Factor VIII from the elution buffer.

3. A method of claim 1 wherein the elution buffer is a salt elution buffer.

4. A method of claim 1 wherein the depth filter is positively-charged.

5. A method of claim 1 wherein the Factor VIII is recombinantly-produced.

6. A method of manufacturing and recovering a protein of interest comprising:
    recombinantly producing a protein of interest using a host cell within a medium, wherein the protein of interest is Factor VIII;
    filtering the medium using a depth filter;
    creating a chromatographic column wherein the depth filter is treated as a stationary phase;
    exposing the depth filter to an elution buffer having a conductivity of at least 20 mS/cm to release the Factor VIII from the depth filter;
    recovering released Factor VIII from the elution buffer; and
    recovering further Factor VIII from the sample passed through the depth filter.

7. A method of claim 6 wherein the elution buffer is a salt elution buffer.

8. A method of claim 6 wherein the filter is positively-charged.

9. A method of claim 6 further comprising:
    combining the Factor VIII recovered from the elution buffer and the Factor VIII recovered from the sample passed through the depth filter into a pharmaceutical composition with pharmaceutically acceptable carriers.

10. A method of manufacturing a pharmaceutical composition comprising:
- recombinantly producing a therapeutic protein of interest using a host cell within a medium, wherein the therapeutic protein is Factor VIII;
- filtering the medium using a CUNO depth filter with a positive charge;
- creating a chromatographic column where in the CUNO depth filter is treated as a stationary phase;
- exposing the CUNO depth filter to a salt elution buffer with a conductivity of at least 20 mS/cm to release the Factor VIII from the CUNO depth filter;
- recovering released Factor VIII from the salt elution buffer;
- recovering further Factor VIII from the sample passed through the CUNO depth filter;
- combining recovered Factor VIII with pharmaceutically acceptable carriers thereby forming the pharmaceutical composition.

11. A method of claim 10 wherein the salt elution buffer has a conductivity of at least 30 mS/cm.

12. A method of claim 10 wherein the salt elution buffer has a conductivity of at least 50 mS/cm.

13. A method of claim 10 wherein the Factor VIII is recombinantly-produced.

* * * * *